US008834979B2

(12) United States Patent
Piranda

(10) Patent No.: US 8,834,979 B2
(45) Date of Patent: Sep. 16, 2014

(54) BAG FOR FORMING AN IMPLANTABLE ARTIFICIAL ORGAN

(75) Inventor: Serge Piranda, Besancon (FR)

(73) Assignee: Statice Sante, Besancon (FR)

( * ) Notice: Subject to any disclaimer, the term of this patent is extended or adjusted under 35 U.S.C. 154(b) by 74 days.

(21) Appl. No.: 13/811,601

(22) PCT Filed: Jul. 6, 2011

(86) PCT No.: PCT/FR2011/051607
§ 371 (c)(1),
(2), (4) Date: May 10, 2013

(87) PCT Pub. No.: WO2012/010767
PCT Pub. Date: Jan. 26, 2012

(65) Prior Publication Data
US 2013/0216746 A1  Aug. 22, 2013

(30) Foreign Application Priority Data
Jul. 22, 2010 (FR) ...................................... 10 56004

(51) Int. Cl.
*A61F 2/04* (2013.01)
*A61F 2/00* (2006.01)
*A61F 2/02* (2006.01)
*C12M 3/00* (2006.01)
*C12M 1/00* (2006.01)

(52) U.S. Cl.
CPC ... *A61F 2/04* (2013.01); *A61F 2/00* (2013.01); *A61F 2/02* (2013.01); *A61F 2/022* (2013.01); *A61F 2002/0081* (2013.01); *A61F 2002/0086* (2013.01); *C12M 21/08* (2013.01); *C12M 23/14* (2013.01)
USPC .......... 428/35.2; 428/131; 428/132; 424/422; 424/424; 424/423; 424/425; 623/11.11; 623/23.71

(58) Field of Classification Search
CPC ................ A61F 2/04; A61F 2/00; A61F 2/02
USPC ......... 428/35.2, 131, 132; 424/422, 424, 423, 424/425; 623/11.11, 23.71
See application file for complete search history.

(56) References Cited

U.S. PATENT DOCUMENTS

| 4,323,457 A | 4/1982 | Sun et al. |
| 5,262,055 A | 11/1993 | Bae et al. |
| 6,372,244 B1 | 4/2002 | Antanavich et al. |
| 7,056,726 B2 | 6/2006 | Legeay et al. |

FOREIGN PATENT DOCUMENTS

| EP | 0 664 729 B1 | 1/1998 |
| FR | 2 384 504 A1 | 10/1978 |
| WO | WO 94/18906 A1 | 9/1994 |
| WO | WO 02/060409 A1 | 8/2002 |
| WO | WO 2008/079997 A2 | 7/2008 |

*Primary Examiner* — Michael C Miggins
(74) *Attorney, Agent, or Firm* — Patterson Thuente Pedersen, P.A.

(57) ABSTRACT

A pouch for forming an implantable artificial organ, including a closed shell provided in a semi-pervious membrane. The pouch further includes a sheet contained within the shell, the sheet including projections on the surface thereof for maintaining a space for cells between the sheet and the shell.

14 Claims, 3 Drawing Sheets

BAG FOR FORMING AN IMPLANTABLE ARTIFICIAL ORGAN

PRIORITY CLAIM

The present application is a National Phase entry of PCT Application No. PCT/FR2011/051607, filed Jul. 6, 2011, which claims priority from French Application No. 1056004, filed Jul. 22, 2010, the disclosures of which are hereby incorporated by reference herein in their entirety.

FIELD OF THE INVENTION

The present invention relates to a pouch for forming an implantable artificial organ such as a pancreas.

BACKGROUND

The first attempts to produce an implantable artificial organ in humans or animals took place a number of decades ago. The objective is to replace a missing organ with a device containing cells satisfying at least one function of said organ while avoiding the constraints of a transplant.

Document FR 2 384 504 already proposes an artificial pancreas supplied with a body fluid to be treated. The fluid passes through a serpentine element housed in a chamber that contains pancreatic islets. The wall of the serpentine element is made of a material that enables exchanges of molecules of low molecular weight such as insulin and glucose, but that forms a barrier to larger molecules such as antibodies and antigens. However, such a device is not implantable.

An implantable artificial organ was proposed by document WO 94/18906. Cells are contained in an envelope made of a semi-permeable membrane, which envelope is contained in another container providing mechanical protection of the first envelope. The cells are, for example, thyroid cells, parathyroid gland cells, adrenal gland cells, liver cells or pancreas cells. The replacement of the cells requires complete replacement of the device.

Document EP 664 729 proposes an implantable and refillable artificial pancreas.

Semi-permeable membranes have been the subject of numerous much research projects. Document WO 02/060409 proposes, for example, a semi-permeable membrane for encapsulating cells made of porous polycarbonate and surface-treated with a hydrophilic polymer. These membranes have the expected characteristics, namely good control of permeability, allowing the nutrients and substances generated by the cells of the artificial organ to quickly pass, limited adhesion of the cells on the surface of the membrane so as not to hinder the exchanges, good mechanical resistance and impermeability to large molecules. However, pouches made of this material do not control the distribution of the islets inside. Masses may form, which then have trouble exchanging nutrients and substances produced.

Accordingly, there is a need for a pouch for forming an implantable artificial organ that ensures good distribution of active cells and that is resistant during and after implantation of the pouch.

SUMMARY OF THE INVENTION

With these objectives in view, the present invention relates to a pouch for forming an implantable artificial organ comprising a closed envelope made of a semi-permeable membrane, characterized in that it comprises a sheet contained in the envelope, the sheet comprising, at its surface, protuberances so as to maintain a space for cells between the sheet and the envelope.

The cells of the artificial organ can thus be housed between the protuberances over the entire surface of the sheet without being compressed by the envelope against the sheet. It is noted that the cells do not form masses and retain a large exchange surface, thereby guaranteeing their durability.

The sheet comprises, for example, protuberances on both of its faces.

According to a particular embodiment, the protuberances have the shape of dashes spaced apart from one another and forming regularly distributed lines parallel to one another. This arrangement defines channels in the direction in which the fluids may easily circulate, channels being oriented, for some, in the direction of the dashes, and, for others, obliquely with respect to said dashes.

According to another embodiment, the pouch comprises at least one connector comprising a body attached to the sheet, and a conduit connected to the connector so as to be in hydraulic communication with the inside of the pouch. It is thus possible to fill or empty the pouch. The attachment of the connector to the sheet makes it possible for the envelope to be protected from stresses that may occur between the pouch and the conduit, because the stresses are taken up by the sheet. The sheet can be mechanically reinforced, while the envelope preserves its thinness necessary for ensuring its semi-permeability.

In one embodiment, the pouch also comprises an implantable percutaneous chamber connected to the conduit so that the implantable percutaneous chamber is in hydraulic communication with the inside of the pouch. The implantable percutaneous chamber is a closed receptacle placed under the skin of a person or an animal and that can be accessed by a needle through the skin and a septum of the chamber. Thus, the contents of the pouch can be renewed usually without the skin being passed through by a conduit.

In particular, the connector can comprise a base, the sheet being clamped between the base and the body in order to attach the connector to the sheet. The clamping makes it possible to obtain a mechanical connection that does not weaken the sheet at the junction.

In one particular embodiment, pouch comprises at least two connectors, one of which comprises a grid inserted in the hydraulic passage. It is thus possible to establish circulation between the two connectors so as to ensure the renewal of the contents of the pouch. The presence of a grid makes it possible to retain the cells if they are to be kept in the pouch. For this, the connector with a grid is used for the suction. If the cells are to be renewed, circulation is established in the opposite direction so that the cells will be discharged by means of the connector without a grid.

The connector can comprise a cap, an upper membrane of the envelope being clamped between the body and the cap so that the connector passes tightly through the upper membrane. Here as well, the clamping technique makes it possible to pass through the envelope without any risk of damage to it.

The sheet is, for example, made of silicone. This material has good properties of flexibility, resistance to stretching, and receptiveness to cells to be contained in the pouch.

In another embodiment, the silicone sheet has a surface treatment of the SI-HPMC-CMC type. SI refers to silicone, HPMC refers to hydroxypropyl-methylcellulose and CMC refers to carboxymethyl cellulose. This treatment makes it possible to increase the biocompatibility properties of the pouch.

In another embodiment, the sheet comprises a textile reinforcement core. This core is, for example a polyester fabric. It makes it possible to control the possible elongation of the sheet under stress, in particular for stresses transmitted by the connectors.

The envelope can be formed by two membranes heat-sealed together. The method for forming the envelope is simple and makes it possible to enclose the sheet in the envelope. The pouch may comprise a silicone frame covering the seam. The frame prevents or inhibits the heat-sealed edges from aggravating the tissue surrounding the pouch.

In another embodiment, the pouch also comprises a permeable over-envelope surrounding the envelope. Thus protection of the envelope made of semi-permeable material is provided without limiting the exchanges between the tissues surrounding the pouch and the inside of it. This protection is particularly useful during the implantation phase in which the risks of tearing are high.

DETAILED DESCRIPTION

Figure 1:
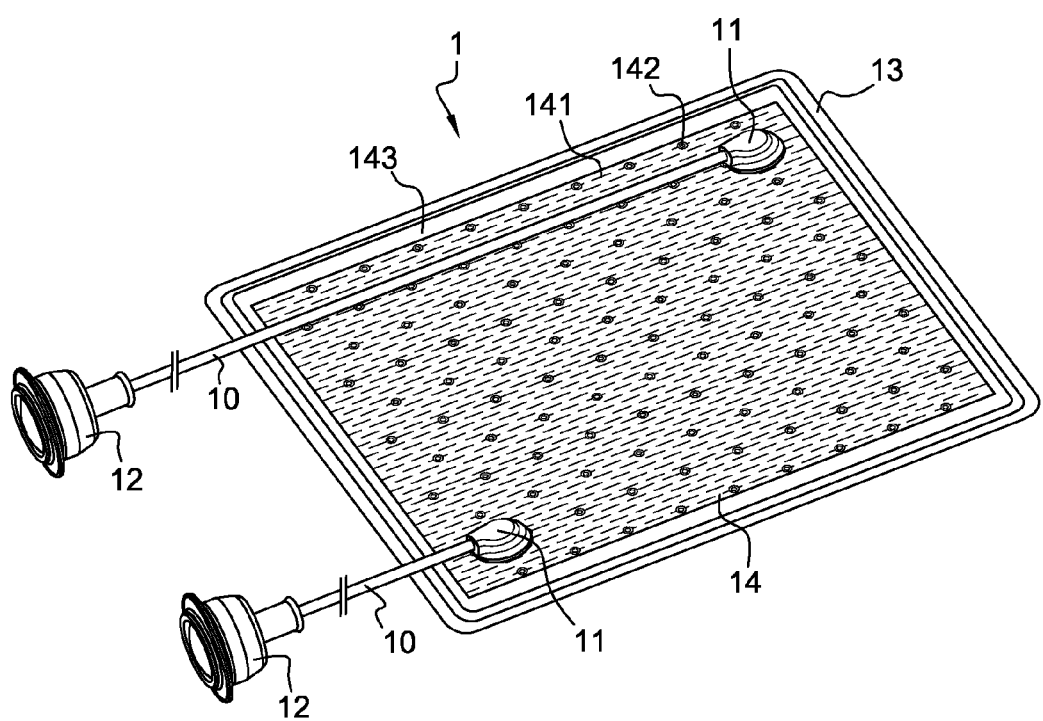
FIG. 1 is a perspective view of a pouch according to one embodiment of the invention.
Figure 2:
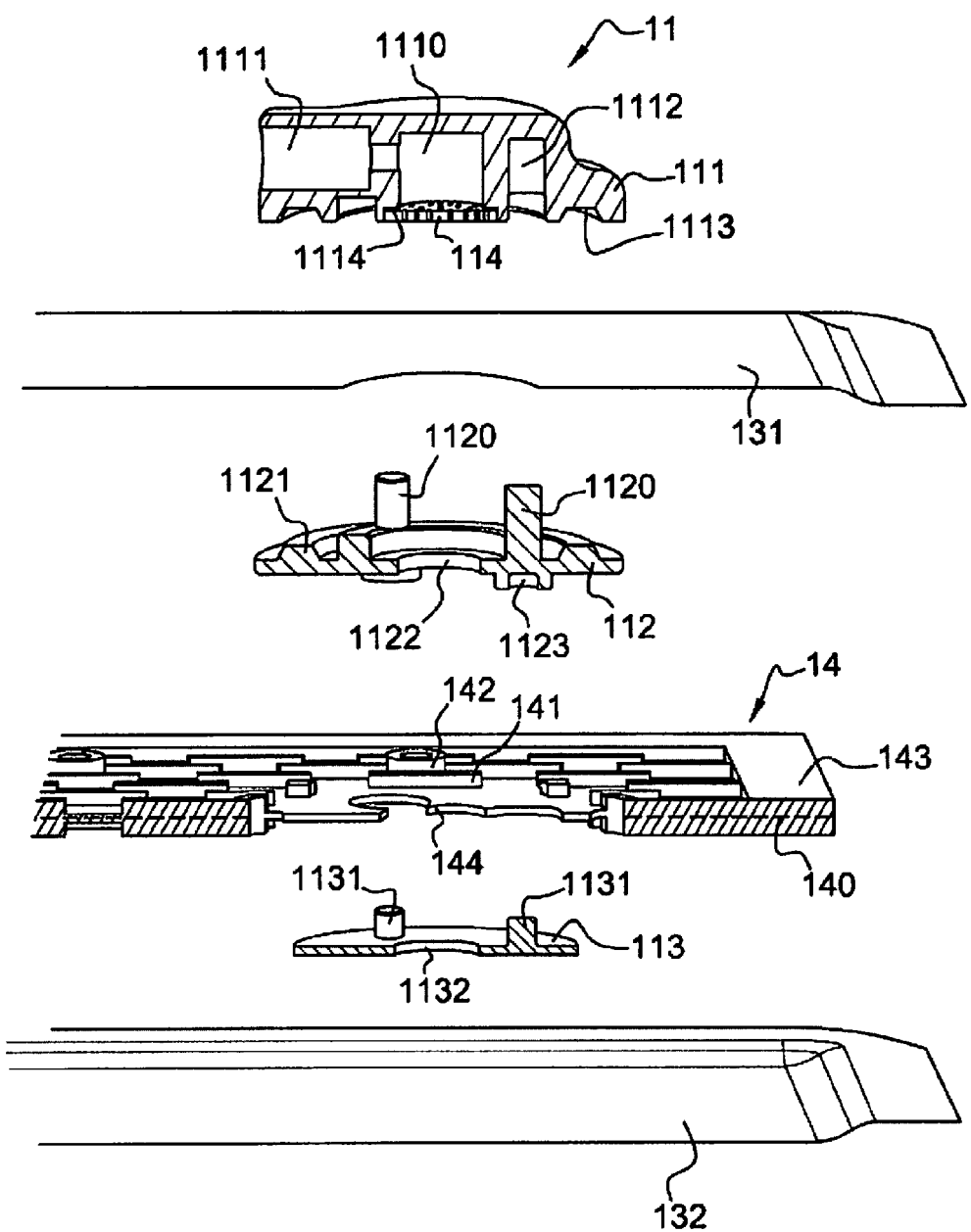
FIG. 2 is a perspective and exploded cross-section view of the pouch of FIG. 1 at a connector.

A pouch 1, according to one embodiment of the invention shown in FIGS. 1 to 4, has a general planar rectangular shape. As shown in FIG. 1, the pouch 1 has two conduits 10 extending from two connectors 11 to two implantable percutaneous chambers 12.

The pouch 1 comprises an envelope 13 containing a sheet 14. The envelope 13 is formed by two membranes 131, 132 made of thermoplastic material sealed together along their edges. The dimensions of the sheet 14 are adjusted so that the sheet is contained within the envelope 13 when flattened. The surface of the sheet 14 is, for example, 50 to 200 cm².

The sheet 14 is produced by molding a silicon-based elastomer material. It comprises a polyester textile core 140 that is over-molded. It comprises, on its two faces, protuberances 141 shaped as dashes spaced apart from one another and forming lines regularly distributed parallel to one another. Aside from the protuberances 141, the sheet 14 has a thickness of between 0.2 to 0.6 mm. The dashes 141 have, for example, a length of 1 to 5 mm, and the lines are spaced apart by a distance of 1 to 2 mm. The interval between the dashes is, for example, 1 to 2 mm. Locally, the dashes 141 are reinforced by rings 142 having a diameter of around 1 mm. The height of the protuberances 141 is, for example 0.2 to 0.8 mm. The periphery of the sheet 14 comprises a bead 143 of the same height as the protuberances 141. The surface of the sheet 14 is treated by a SI-HPMC-CMC coating, which reduces the surface tension of the sheet 14 in order to reduce the adhesion of the cells to the sheet 14 and reduce the secretion of proinflammatory mediators.

The two membranes 131, 132 forming the envelope 13 are semi-permeable so as to enable the transfer of small molecules but stop the large molecules, such as, for example, polycarbonate membranes as described in document WO 02/060409. The two membranes 131, 132 are heat-sealed at their periphery to form the envelope 13.

A frame 130 made of silicon has a U-shaped cross-section and surrounds the periphery of the envelope 13 so as to cover the seam of the two membranes 131, 132.

Hydraulic communication is established between the implantable percutaneous chambers 12 by the two conduits 10 by passing through the inside of the envelope 13. For this, each conduit 10 is connected to a connector 11, which produces the passage between the inside and the outside of the envelope 13.

Each connector 11 comprises a cap 111, a body 112 and a base 113. One of the two connectors 11 also comprises a filtration grid 114. The cap 111 comprises a central cavity 1110 connected to a sleeve 1111, which receives the conduit 10. The conduit 10 is, for example, bonded to the inside of the sleeve 1111. The body 112 has an annular shape and comprises three body teats 1120 projecting toward the cap 111. The cap 111 comprises three holes 1112 opposite the body teats 1120 so as to produce an assembly between the body 112 and the cap 111 by fitting the body teats 1120 into the holes 1112. The body 112 also comprises an annular bulge 1121 corresponding to a recess 1113 of complementary shape produced in the cap 111, so as to clamp and hold one of the membranes 131, called an upper membrane, between the cap 111 and the body 112. In this location, the upper membrane 131 is drilled so as to allow the body teats 1120 to pass through. The central opening 1122 of the body 112 is opposite the central cavity 1110 of the cap 111 so that hydraulic communication can be established between them. If a grid 114 is present, it is housed in a shoulder 1114 of the cap 111, where the central cavity 1110 opens toward the body 112.

Figure 3:
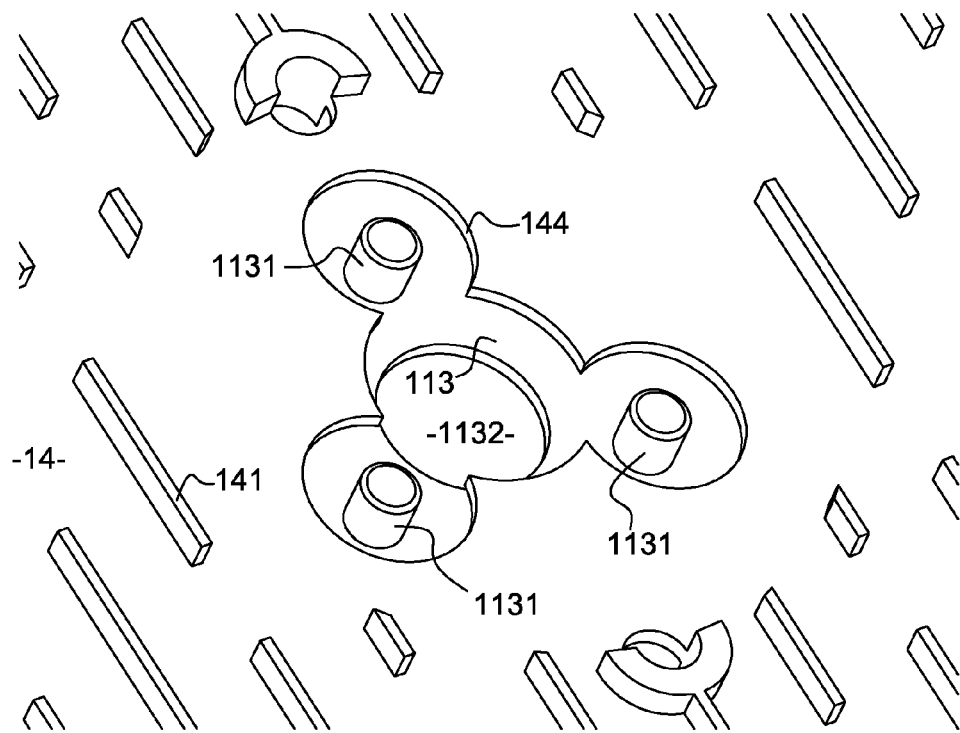
FIG. 3 is a partial perspective view of the pouch at a connector and representing the sheet and the base of a connector.
Figure 4:
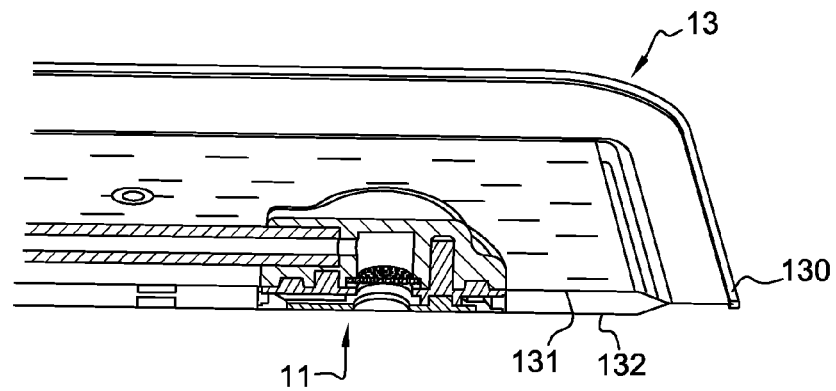
FIG. 4 is a cross-section view of the connector of the pouch of FIG. 1 in the assembled position.

The base 113 also has a planar annular shape and comprises three base teats 1131 projecting toward the body 112 so as to be fitted into the corresponding holes 1123 of the body 112. This makes it possible to clamp the sheet 14 between the base 113 and the body 112. To do this, the sheet 14 comprises a cut 144 corresponding to the three base teats 1131 and to the central opening 1122 of the body 112. The protuberances 141 are also interrupted so as to enable planar support of the clamping area between the body 112 and the base 113, as shown by FIG. 3. The central opening 1132 of the base 113 is also opposite the central cavity 1110 of the cap 111 so as to establish hydraulic communication between them.

The teats 1120, 1131 receive, for example, adhesive in order to produce the permanent assembly of parts 111, 112, 113 with one another. In another embodiment, the fitting may be forced or conical, or the teats may be welded by ultrasound.

The components 111, 112, 113 of the connector 11 are produced by plastic polypropylene injection. They may receive a surface treatment so as to increase biocompatibility.

The assembly of the pouch 1 is produced as follows. The base 113 of each connector 11 is placed under the sheet 14. The body 112 of each connector 11 is placed above the sheet 14 and assembled with the corresponding base 113 by clamping the sheet 14. The membranes 131, 132 are placed below and above the sheet 14, then they are sealed together at the edges. The frame 130 is placed by bonding in order to cover these seams. The cap 111 of the connectors 11 is placed above the upper membrane 131 and assembled with the corresponding body 112 by clamping the upper membrane 131 between the recess 1113 and the bulge 1121. As the case may be, the grid 114 is placed in the shoulder 1114 of the cap 111 before assembly with the body 112. The conduits 10 are connected to the caps 111 and to the implantable percutaneous chambers 12.

During use of the pouch 1, it is rolled up if necessary and inserted into a body through a small incision, then unrolled. The implantable percutaneous chambers 12 are also inserted and placed under the skin. When it is certain that the pouch 1 is well tolerated by the receiving body, the cells are introduced with a syringe by the implantable percutaneous chamber 12 connected to the connector 11 without a grid. The elements introduced pass into the implantable percutaneous chamber 12, then into the conduit 10, into the central cavity 1110 of the cap 111, through the openings of the membrane and the body 112, then through the cut 144 of the sheet 14. The cells are distributed in the pouch 1 and are housed between the protuberances 141. Optionally, fluid circulation is established by suction through the other implantable percutaneous chamber 12.

The invention is not limited to the example described above. The pouch may be disc-shaped or have any planar shape. The protuberances may be in the shape of pins, bosses, rings or cones. The connectors 11 may be made of biocompatible materials other than polysulfone or polycarbonate. A permeable over-envelope may surround the envelope. The frame 130 is not essential, in particular if an over-envelope is present.

The invention claimed is:

1. A pouch for forming an implantable artificial organ, the pouch comprising:
   a closed envelope made of a semi-permeable membrane; and
   a sheet contained within the envelope, the sheet including, extending from at least one surface or face of the sheet, protuberances so as to maintain a space for cells between the sheet and the envelope.

2. The pouch according to claim 1, wherein the sheet comprises a textile reinforcement core.

3. The pouch according to claim 1, wherein the pouch further comprises a permeable over-envelope surrounding the envelope.

4. The pouch according to claim 1, wherein the sheet presents two faces, and wherein the sheet comprises protuberances extending from both of the faces.

5. The pouch according to claim 4, wherein the protuberances have the shape of dashes spaced apart from one another and forming regularly distributed lines parallel to one another.

6. The pouch according to claim 1, wherein the pouch further comprises at least one connector comprising a body attached to the sheet, and a conduit connected to the connector so as to be in hydraulic communication with the inside of the pouch.

7. The pouch according to claim 6, wherein the pouch further comprises an implantable percutaneous chamber connected to the conduit so that the implantable percutaneous chamber is in hydraulic communication with the inside of the pouch.

8. The pouch according to claim 6, wherein the connector further comprises a base, the sheet being clamped between the base and the body in order to attach the connector to the sheet.

9. The pouch according to claim 6, wherein the pouch further comprises at least two connectors, one of which comprises a grid inserted in the hydraulic passage.

10. The pouch according to claim 6, wherein the connector further comprises a cap, an upper membrane of the envelope being clamped between the body and the cap so that the connector passes tightly through the upper membrane.

11. The pouch according to claim 1, wherein the sheet is made of silicone.

12. The pouch according to claim 11, wherein the silicone sheet has a surface treatment of the SI-HPMC-CMC type.

13. The pouch according to claim 1, wherein the envelope is formed by two membranes heat-sealed together.

14. The pouch according to claim 13, wherein the pouch comprises a silicone frame covering the seam.

* * * * *